(12) United States Patent
Bumiller et al.

(10) Patent No.: US 9,317,698 B2
(45) Date of Patent: *Apr. 19, 2016

(54) SYSTEM AND METHOD FOR PROVIDING INFORMATION ACCESS ON A PORTABLE DEVICE

(71) Applicant: BlackBerry Limited, Waterloo (CA)

(72) Inventors: George Baldwin Bumiller, Ramsey, NJ (US); Michael J. Crowley, Haslet, TX (US); Luis Estable, Gatineau (CA)

(73) Assignee: BlackBerry Limited, Waterloo, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/956,072

(22) Filed: Jul. 31, 2013

(65) Prior Publication Data

US 2013/0318621 A1 Nov. 28, 2013

Related U.S. Application Data

(63) Continuation of application No. 13/616,297, filed on Sep. 14, 2012, now Pat. No. 8,521,126, which is a continuation of application No. 11/457,252, filed on Jul. 13, 2006, now Pat. No. 8,275,345.

(60) Provisional application No. 60/792,918, filed on Apr. 18, 2006.

(51) Int. Cl.
*H04M 11/04* (2006.01)
*G06F 21/60* (2013.01)
(Continued)

(52) U.S. Cl.
CPC .............. *G06F 21/60* (2013.01); *G06F 19/323* (2013.01); *H04M 1/72541* (2013.01); *H04W 76/007* (2013.01); *H04M 11/04* (2013.01); *H04W 4/00* (2013.01); *H04W 88/02* (2013.01)

(58) Field of Classification Search
CPC ..... H04W 76/007; H04W 4/22; H04W 12/06; H04M 11/04
USPC ................... 455/404.1, 404.2, 411; 379/37
See application file for complete search history.

(56) References Cited

U.S. PATENT DOCUMENTS 5,742,666 A   4/1998   Alpert
5,933,080 A   8/1999   Nojima
(Continued)

FOREIGN PATENT DOCUMENTS

CA   2691345   7/2010
CN   1520132   8/2004
(Continued)

OTHER PUBLICATIONS

Office Action dated Mar. 6, 2014 from corresponding U.S. Appl. No. 13/542,385.

(Continued)

*Primary Examiner* — Danh Le
(74) *Attorney, Agent, or Firm* — Fish & Richardson P.C.

(57) ABSTRACT

A system and method of providing information stored in a memory is provided. The system comprises an information repository for storing information and an access module for providing access to the information in response to a predetermined operation performed on a man-machine interface. The method includes the steps of storing information in a memory and providing access to the information in dependence upon at least one predetermined operation.

21 Claims, 13 Drawing Sheets

(51) Int. Cl.
*G06F 19/00* (2011.01)
*H04M 1/725* (2006.01)
*H04W 76/00* (2009.01)
*H04W 4/00* (2009.01)
*H04W 88/02* (2009.01)

(56) References Cited

U.S. PATENT DOCUMENTS

| | | | |
|---|---|---|---|
| 6,574,484 | B1* | 6/2003 | Carley .......................... 455/521 |
| 7,466,235 | B1 | 12/2008 | Kolb |
| 7,689,209 | B1 | 3/2010 | Spitz et al. |
| 7,983,663 | B2 | 7/2011 | Siu |
| 2002/0131330 | A1 | 9/2002 | Zion et al. |
| 2003/0076932 | A1 | 4/2003 | Andrew |
| 2003/0104790 | A1 | 6/2003 | Ylitalo |
| 2004/0024706 | A1 | 2/2004 | Leduc |
| 2004/0103000 | A1 | 5/2004 | Owurowa et al. |
| 2004/0203576 | A1* | 10/2004 | Droste et al. ............... 455/404.1 |
| 2004/0203622 | A1 | 10/2004 | Esque et al. |
| 2005/0085215 | A1* | 4/2005 | Kokko et al. ............... 455/404.1 |
| 2005/0151642 | A1 | 7/2005 | Tupler et al. |
| 2005/0193144 | A1* | 9/2005 | Hassan et al. .................. 709/238 |
| 2006/0026689 | A1 | 2/2006 | Barker et al. |
| 2006/0079269 | A1 | 4/2006 | Sorotzkin |
| 2006/0142057 | A1 | 6/2006 | Schuler et al. |
| 2006/0172720 | A1 | 8/2006 | Islam et al. |
| 2006/0293029 | A1* | 12/2006 | Jha et al. ........................ 455/411 |
| 2007/0102527 | A1 | 5/2007 | Eubank et al. |
| 2007/0117574 | A1 | 5/2007 | Watanabe |
| 2007/0135043 | A1* | 6/2007 | Hayes et al. .................. 455/26.1 |
| 2007/0200734 | A1* | 8/2007 | Lee et al. ......................... 341/22 |
| 2007/0243853 | A1 | 10/2007 | Bumiller |
| 2008/0005301 | A1 | 1/2008 | Li |
| 2008/0070546 | A1 | 3/2008 | Lee |
| 2008/0080687 | A1 | 4/2008 | Broms |
| 2008/0166992 | A1 | 7/2008 | Ricordi |
| 2008/0284587 | A1 | 11/2008 | Saigh |
| 2009/0005068 | A1 | 1/2009 | Forstall et al. |
| 2009/0047923 | A1 | 2/2009 | Jain et al. |
| 2009/0164467 | A1 | 6/2009 | Ala-Lahti |
| 2009/0205041 | A1 | 8/2009 | Michalske |
| 2010/0069099 | A1 | 3/2010 | Dunn et al. |
| 2010/0190467 | A1 | 7/2010 | Scott et al. |
| 2011/0041102 | A1 | 2/2011 | Kim |
| 2011/0088003 | A1 | 4/2011 | Swink et al. |
| 2011/0159844 | A1 | 6/2011 | Gillet et al. |

FOREIGN PATENT DOCUMENTS

| | | |
|---|---|---|
| DE | 100 64 978 C1 | 7/2002 |
| DE | 10064978 | 7/2002 |
| DE | 103 23 582 A1 | 12/2004 |
| DE | 10323582 | 12/2004 |
| EP | 1170969 A1 | 1/2002 |
| EP | 1361774 | 11/2003 |
| EP | 2214385 | 8/2010 |
| GB | 2401285 | 11/2004 |
| JP | 03-179938 | 8/1991 |
| JP | 07-147694 | 6/1995 |
| JP | 11-339171 | 12/1999 |
| JP | 2000-261573 | 9/2000 |
| JP | 2001-320467 | 11/2001 |
| JP | 2001-326970 | 11/2001 |
| JP | 2004-120467 | 4/2004 |
| JP | 2004-511923 | 4/2004 |
| JP | 2004511923 | 4/2004 |
| JP | 2005-020109 | 1/2005 |
| JP | 2005-026827 | 1/2005 |
| WO | 01/41458 | 6/2001 |
| WO | 0141458 | 6/2001 |
| WO | 2004/054278 A2 | 6/2004 |
| WO | 2004051976 | 6/2004 |
| WO | 2004054278 | 6/2004 |
| WO | 2004/082190 A2 | 9/2004 |
| WO | 2004/104898 | 12/2004 |
| WO | 2005053337 | 6/2005 |
| WO | 2005/069676 | 7/2005 |
| WO | 2006135120 | 12/2006 |
| WO | 2007118331 | 10/2007 |

OTHER PUBLICATIONS

"3rd Generation Partnership Project; Technical Specification Group Services and System Aspects; Man-Machine Interface (MMI) of the User Equipment (UE) (Release 7)," 3GPP TS 22.030 v7.0.1 (Jul. 2005).

"I.C.E. (In Case of Emergency) Initiative [Edited]," Cingular Customer Forums, Aug. 4, 2005, Retrieved from http://forums.cingular.com/cng/board/message?board.id=announcements&message.id=206.

"Ice Your Cell Phone for Safety," CBS News, London, Jul. 26, 2005, CBS Broadcasting, Inc., Retrieved from www.cbsnews.com/stories/2005/07/26/earlyshow/printable711715.shtml.

"ICE," Retrieved from http://www.ci.miramar.fl.us/fire/ice.htm on Mar. 31, 2006.

Advisory Action for U.S. Appl. No. 12/361,116 dated Nov. 14, 2011 (3 pages).

Chaves, Susan, "ICE First application turns cell phones into lifesavers," The Darien Time, Darien, Connecticut, Mar. 16, 2006, Retrieved from http://www.acorn-online.com/news/publish/article_5358.shtml.

Chinese Office Action (with translation) for Chinese Application No. 200780022704.7 dated Feb. 29, 2012 (15 pages).

Coates, Sam, "ICE Cell Phone Plan Would Help Rescurers; Idea to Designate Next of Kin in Electronic Address Book is Gaining Popularity; [Final Edition]," The Washington Post, Jul. 18, 2005, p. A.06, Washington, D.C.

English-language translation of Korean Office Action that issued on Mar. 25, 2010 from corresponding Korean Patent Application No. 10-2008-7027918.

European Search Report for EP Application No. 09151567.6 dated May 14, 2009.

European Search Report for EP Application No. 09151568.4 dated Jun. 7, 2010 (5 pages).

European Search Report for EP Application No. 09151569.2 dated May 13, 2009.

Extended European Search Report dated Jul. 6, 2009, issued in reference to European Patent Application No. 09151568.4.

Extended European Search Report dated May 20, 2009, issued in reference to European Patent Application No. 09151567.6.

Extended European Search Report dated May 20, 2009, issued in reference to European Patent Application No. 09151569.2.

Extended European Search Report for EP 09151568.4 dated Jul. 6, 2009 (9 pages).

Hallburn, Mark, "Putnam county Debuts ICE Program," Putnamlive.com, Retrieved from the Internet URL:http://web.archive.org/web/20051210102349/http://putnamlive.com/PutnamCountyDebutsICEProgram.html.

Hibbert, David, "Help Out in a Crisis—With ICE," Lockergnome LLC, Jul. 14, 2005, Retrieved from www.channels.lockergnome.com/mobile/archives/20050714_help_out_in_a_crisis_with_ice.phtml.

MacInnes, Alexander, "Safety campaign urges storing contact numbers on cellphones," Herald News, Aug. 3, 2005, North Jersey Media Group (2005), Retrieved from www.northjersey.com.

Meyers, Michelle, "ICE your cell phone," CNET News.com, Jul. 19, 2005, Retrieved from http://news.com.com/2061-10800 3-5795310.html.

Morrison, Michael, "Blackberry in a SnapR," Jul. 1, 2005, SAMS, XP007904690 ISBN: 0-672-32670-1.

Office Action for U.S. Appl. No. 12/361,052 dated Dec. 1, 2011 (12 pages).

Office Action for U.S. Appl. No. 12/361,052 dated Jun. 30, 2011 (8 pages).

Office Action for related U.S. Appl. No. 12/361,084 dated Jul. 19, 2011 (6 pages).

(56) References Cited

OTHER PUBLICATIONS

Office Action for related U.S. Appl. No. 12/361,084 dated Oct. 3, 2011 (9 pages).
Office Action for related U.S. Appl. No. 12/361,116 dated May 17, 2011 (12 pages).
Office Action for Related U.S. Appl. No. 12/361,116 dated Sep. 27, 2011 (14 pages).
Office Action for U.S. Appl. No. 12/361,084 dated Jan. 12, 2012 (9 pages).
European Office Action for European Application No. 09163500.3 dated Dec. 12, 2012 (6 pages).
U.S. Advisory Action for related U.S. Appl. No. 12/361,052, dated Sep. 10, 2012 (3 pages).
U.S. Advisory Action for related U.S. Appl. No. 12/361,084, dated Feb. 23, 2012 (3 pages).
U.S. Advisory Action for related U.S. Appl. No. 12/361,084, dated Nov. 14, 2012 (2 pages).
U.S. Office Action for related U.S. Appl. No. 12/361,052, dated Apr. 25, 2012 (8 pages).
Zatz, Arline, "Star of Life," Rescue-EMS Magazine, Jul./Aug. 1992, Retrieved from www.angelfire.com/co/fantasyfigures/staroflife.html.
U.S. Office Action for related U.S. Appl. No. 12/361,052, dated Jul. 3, 2012 (9 pages).
U.S. Office Action for related U.S. Appl. No. 12/361,084, dated Aug. 27, 2012 (10 pages).
U.S. Office Action for related U.S. Appl. No. 12/361,084, dated May 15, 2012 (9 pages).
U.S. Office Action for related U.S. Appl. No. 12/361,116, dated Dec. 20, 2012 (15 pages).
U.S. Office Action for related U.S. Appl. No. 13/551,386, dated Dec. 10, 2012 (14 pages).
Notice of Reasons for Rejection mailed Jul. 2, 2013, in corresponding Japanese Patent Application No. 2011-256702, and English language translation thereof (9 pages).
International Search Report and Written Opinion dated Mar. 14, 2013, from related PCT Application No. PCT/CA2012/050487.
Chinese Office Action dated Dec. 3, 2014 from corresponding Chinese Patent Application No. 201210160344.X.
Office Action issued in Japanese Application No. 2011-256702 on Mar. 16, 2015; 3 pages.
Office Action issued in Chinese Application No. 20120160344.X on Jul. 29, 2015; 3 pages.
Office Action issued in Indian Application No. 8983/DELNP/2008 on Mar. 11, 2015; 2 pages.

\* cited by examiner

ICE Display Screens    80

81a → ICE 1 Abigail - wife
      + 1 519 555 1212 cell cycles through
ICE 1 through ICE n 81b → ICE 2 Joseph - son
      + 1 416 555 1212 home 82a → ICE: country : US
      1. Wife
      2. Tour guide
      3. Friend on tour Press Number to select cycles through
ICE 1 through ICE n Allows selection of
any ICE entry with
full details 82b → ICE: country : US
      2. Tauck Tour – Alaska
         Russ Smith, guide
         +1 973 555 1212 cell Press End or ****
      for main menu

Fig. 4b

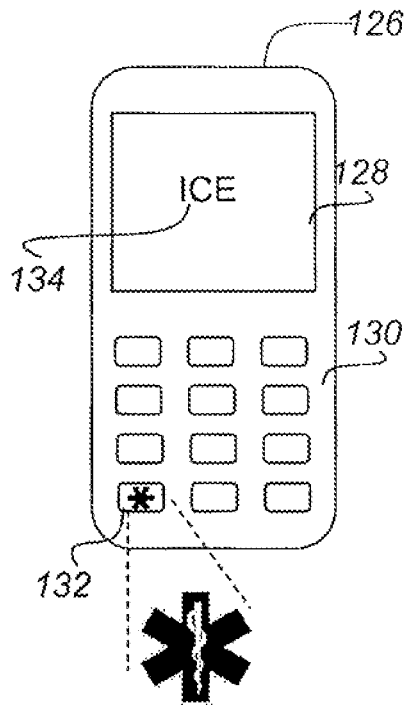
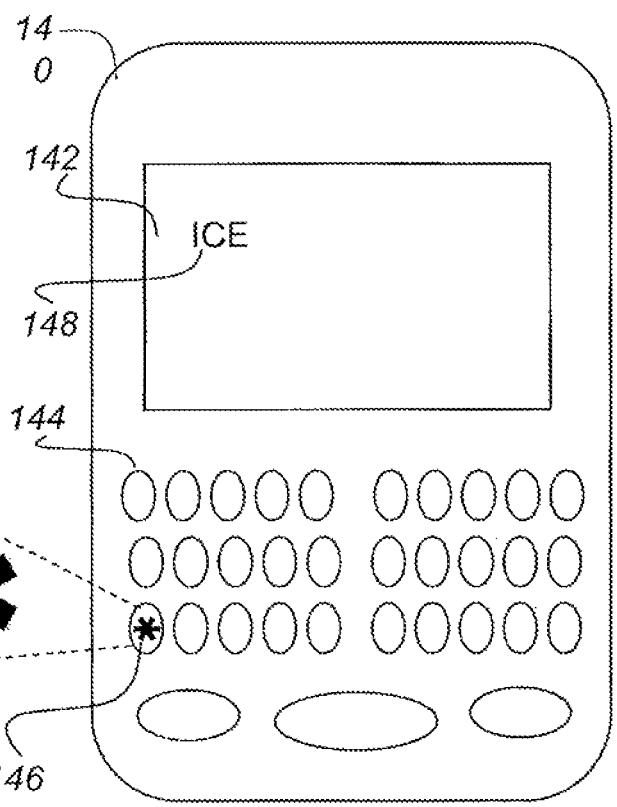
Fig. 7
Fig. 8

SYSTEM AND METHOD FOR PROVIDING INFORMATION ACCESS ON A PORTABLE DEVICE

This application is a continuation of U.S. patent application Ser. No. 13/616,297, filed Sep. 14, 2012, and claims the benefit of U.S. patent application Ser. No. 13/616,297, which is a continuation of U.S. patent application Ser. No. 11/457,252, filed Jul. 13, 2006, now U.S. Pat. No. 8,275,345, which claims the benefit of U.S. Provisional Application No. 60/792,918 filed Apr. 18, 2006, all of which are hereby incorporated by reference in their entirety.

This patent document relates generally to portable devices, and in particular to a system and method of providing information access on such devices.

BACKGROUND

The world presents many hazardous situations to its human inhabitants. Some of these are natural disasters, for example tsunamis, hurricanes, tornadoes, floods and landslides. Others are of man-made origin, for example transportation accidents, acts of wax and terrorism. One common denominator in all of these events is a need to help victims in as timely and effective fashion possible under the circumstances. When impersonal events happen and individuals are injured, the event becomes very personal with access to personal medical information and emergency contacts becomes of paramount importance. In Case of Emergency (ICE) information is crucial to the treatment of disaster and accident victims. Obtaining this information is particularly difficult when the disasters are also responsible for damaging local infrastructure, such as communications systems. Ironically systems most needed during, widespread disasters may also be compromised by those same disasters.

Consequently, there is a need to provide ICE information for individuals that is not dependent upon real-time access to communications infrastructure.

BRIEF DESCRIPTION OF THE DRAWINGS

An embodiment of the patent disclosure will now be described by way of example only with reference to the following drawings in which:

FIGS. 4a and 4b illustrate various display screens, in accordance with an embodiment of the information access system;

FIG. 7 illustrates an example of mobile communications device for providing ICE information, in accordance with an embodiment of the information access system;

FIG. 8 illustrates another example of a mobile communications device for providing ICE information, in accordance with an embodiment of the information access system;

DETAILED DESCRIPTION

Figure 1:
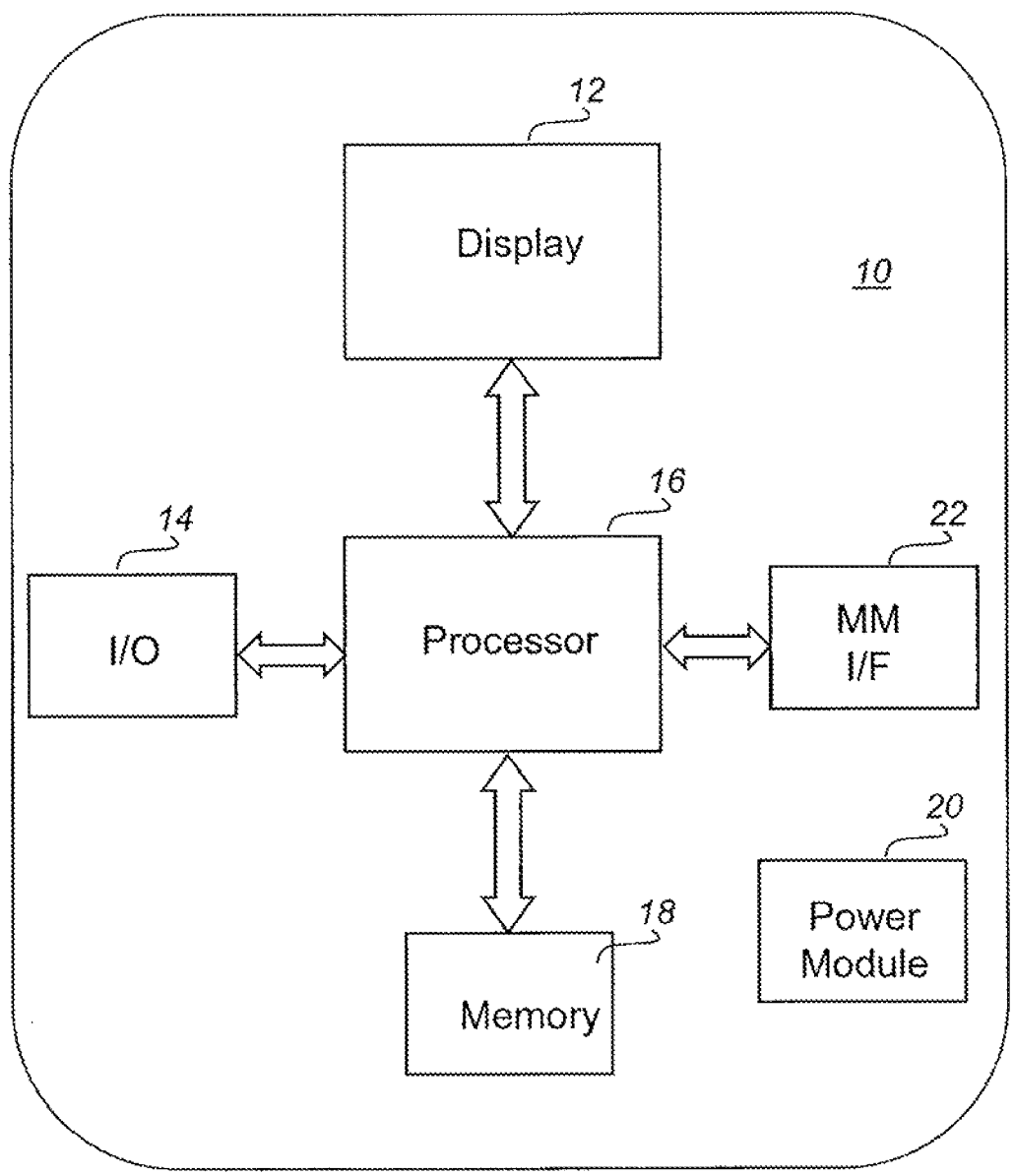
FIG. 1 illustrates an example of a generic portable electronic device.

The patent disclosure describes a solution to one or more of the problems described above. Accordingly, the present disclosure teaches a system and method of providing information access on portable devices.

One thing a great many individuals have, in common is carrying portable electronic devices. For example, there are personal music players, such as Motion Picture Experts Group, Audio Layer 3 (MP3) players, personal data assistants (PDAs), and various wireless devices such as cell phones and electronic mail (email) devices. On any given day, an individual may early several of these devices.

Increasingly manufacturers of portable electronic devices are combining functions of several different devices into a single device. Most recent examples of this are cell phones that include digital camera or MP3 player functions. This trend is expected to continue, with further integration anticipated with each new generation of devices. This trend enhances the likelihood that individuals carry such a device. This integration of features is possible because the current generation of devices have a large number of common components. Such common components include a display screen, an input/output port, a central processor (CPU), a memory, a power module and a tactile man-machine interface.

In accordance with an embodiment of the patent disclosure, there is provided an information access system for providing information. The information access system comprises an information repository for storing information and an access module for providing access to the information.

In accordance with an embodiment of the patent disclosure, there is provided a portable device comprising a display for displaying in case of emergency information, a man-machine interface for receiving requests for the in case of emergency information, a processor coupled to the display and to the man-machine interface and including the access module for accessing in case of emergency information in dependence upon a predetermined operation, and a memory including in case of emergency information.

In accordance with another embodiment of the patent disclosure, there is provided a method of providing information access on a portable device comprising the steps of storing information in a memory and providing access to the information in dependence upon at least one predetermined keystroke.

A system and method of the patent disclosure is now described with reference to various examples of how the embodiments can best be made and used. For convenience, like reference numerals are used throughout the description and several views of the drawings to indicate like or corresponding parts, wherein the various elements are not necessarily drawn to scale.

Referring to FIG. 1 there is illustrated in a component diagram an example a generic portable electronic device 10, in which an embodiment of the present patent disclosure may be implemented. The generic portable device 10 includes a display screen 12, an input/output port 14, a processor 16, a memory 18, a power module 20 and a tactile man-machine interface 22. These components are common to portable electronic devices individuals carry with them on a daily basis. Advantageously, the ubiquitous nature of such devices is used by the present system and method to store ICE information on such devices. Examples of portable devices suitable for storing ICE information are cell phones, wireless data/email devices, PDAs and MP3 players.

Figure 2:
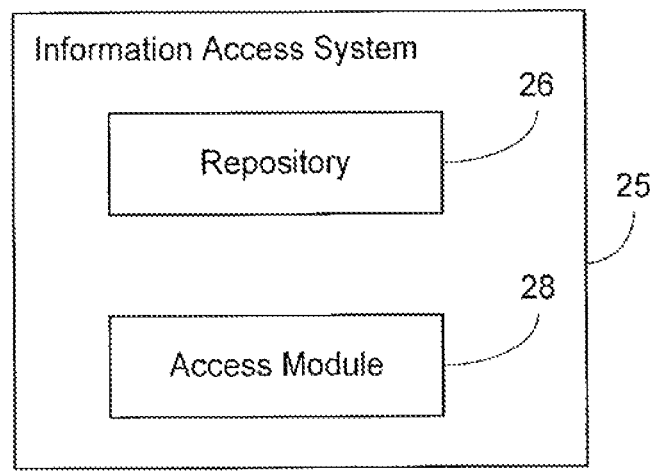
FIG. 2 illustrates in a block diagram an example of an information access system for storing and providing information, in accordance with an embodiment of the present patent disclosure.

Referring to FIG. 2 there is illustrated in a block diagram an example of an information access system 25 for storing and providing information, in accordance with an embodiment of the present patent disclosure. The information access system 25 comprises an information repository 26 for storing information, and an access module 28 for providing access to the information. Other components may be added to the information access system 25. The components of the information access system 25 may be implemented in components of a portable device 10. Information stored in a device may be locked. Such locking of information may include user access to specific information being secured and/or the entire device being secured to all users. Advantageously, a predetermined key stroke may be used to unlock the information. I.e., a locked device may be unlocked to provided the information, or access to information that is secured in an unlocked device may be provided. Examples of locking conditions are further described below.

Preferably, the information access system 25 is used to store and provide access to in case of emergency (ICE) information. The remainder of this disclosure will discuss the invention with respect to ICE information. However, other information may be used in place of ICE information.

The repository 26 can be implemented in memory 18 for ICE information storage on the device 10. Examples of memory in various portable devices include subscriber information module (SIM) cards for wireless terminals with a removable SIM, and mobile equipment (ME) for wireless terminals without a removable SIM or equivalent. The term subscriber information module in this disclosure encompasses SIM, Universal SIM (USIM), Internet Protocol Multimedia Services Identity Module (ISIM), Removable User Identity Module (RUIM) and other removable subscriber information modules. ICE information may also be stored in the ME even when the device uses a SIM card. Such storage in the ME enables the user to change the SIM (for example, when roaming) without loss of ICE information and without the need to immediately download the information to the SIM card. Such storage in the ME also enables the user to have ICE information available if the operator providing the new SIM has not implemented ICE.

Figure 3:
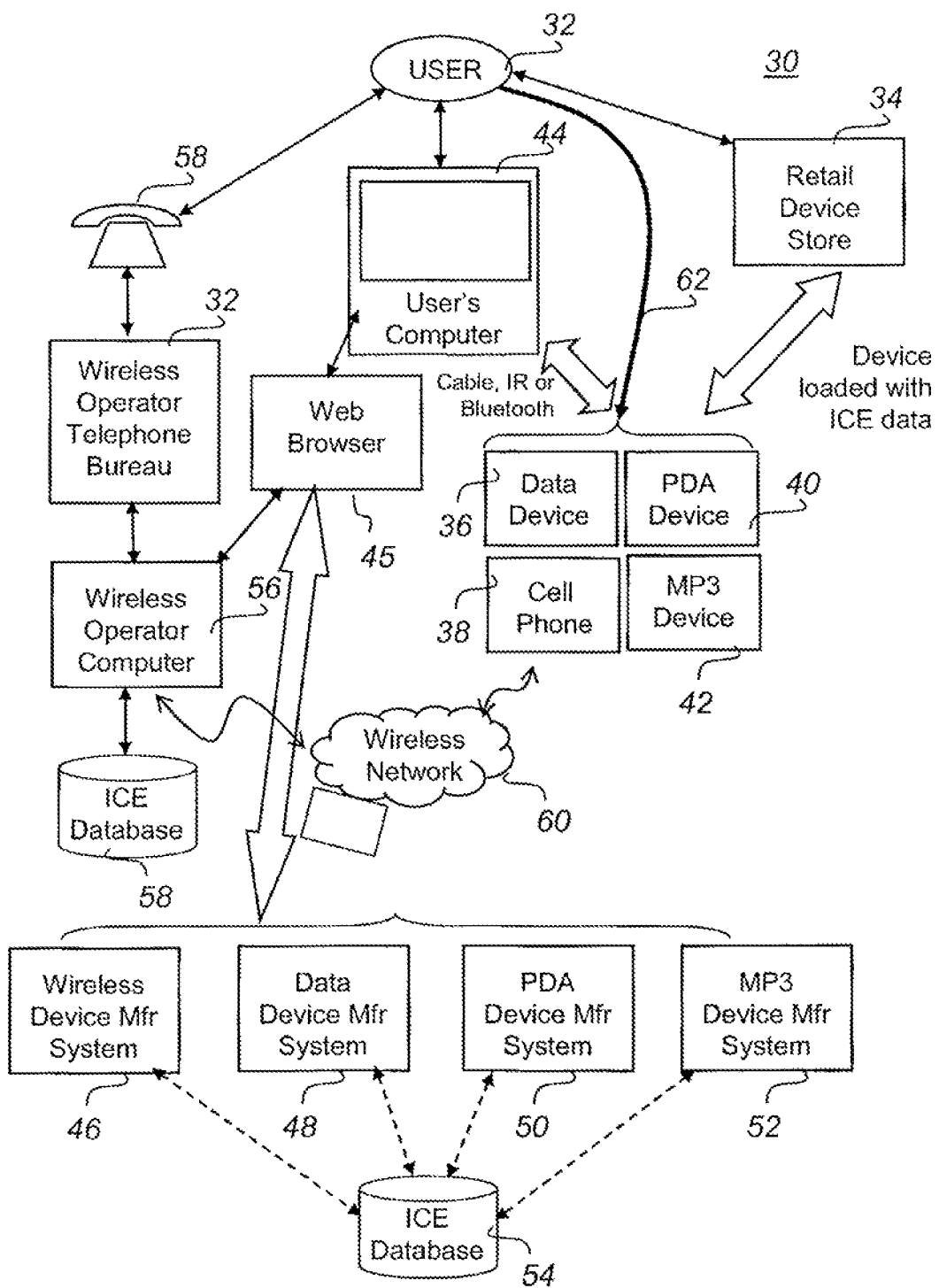
FIG. 3 illustrates in an information flow diagram an example of loading ICE information, in accordance with an embodiment of the information access system.

Referring to FIG. 3 there is illustrated in an information flow diagram an example of loading ICE information (30), in accordance with an embodiment of the ICE system. In the method 30 of FIG. 3 various portable devices are considered for loading ICE information. A user 32 may use any one of a number of different approaches depending upon the type of device and the resources available to the user. In a direct approach, the user 32 takes the device to a retail device store 34 where any device (for example, a data device 36, a cell phone 38, a PDA device 40 or an MP3 device 42) can be directly loaded with ICE information by cable, infrared or Bluetooth™ connection to a computer in the retail device store 34. Similarly the user 32 can add, delete, change or update ICE information on their portable electronics devices 36, 38, 40 or 42.

If the user 32 has a personal computer 44, a connect to the devices via cable, infrared or Bluetooth can be used to load, add, delete, change or update ICE information on their portable electronics devices 36, 38, 40 or 42. A program downloaded from the manufacturer or from the wireless operator to the user's personal computer (PC) enables the user to enter the data and view it, likely in its entirety, on the PC screen. Changes can be made to the data and the ICE information can then be directly downloaded over a cable or Bluetooth from the PC to the device.

In addition to a direct link, a computer 44 can use a web browser 45 to access device manufacturer systems 46, 48, 50 or 52 to load, add, delete, change or update ICE information and have that information stored centrally on a database(s) 54 and on their portable electronics devices 36, 38, 40 or 42. For portable devices with or without a QWERTY keyboard, the use of a computer terminal linked to the operator or manufacturer's computer system provides a very user-friendly way of easily entering the information, and of having the data stored for restoration of ICE information when required. The operator or manufacturer may provide means of adapting the information to other devices with different display characteristics or of assisting the user in adapting the information to other formats.

For portable devices having wireless communication capability, the web browser 45 can be used to access a wireless operator computer to load add, delete, change or update ICE information for the portable electronics devices 36, 38 or 40. Such changes can be stored in a database 58, and then transferred via a wireless network 60 to the portable electronics devices 36, 38 or 40.

Finally, portable devices 36, 38, 40 or 42 having user input interfaces such as keypads, keyboards, touch pads and stylus devices can have ICE information directly input 62. Examples of different terminal keyboard (man-machine interface 22 of FIG. 1) entry include TAP or iTAP method on a cell phone or similar keypad, SureType™ on some BlackBerry™ models, and typing on a QWERTY keyboard.

Synchronizing the ICE information with a central database could then be accomplished using the input/output port that allows them to be linked to a personal computer or wireless interfaces such as Bluetooth that provide a local communications link to the portable device and software resident on the computer 44. Alternatively, for wireless devices, synchronization can be completed via the wireless network 60.

In some cases, for example devices used by children, the individual responsible for the loading of the ICE information could be a parent or guardian rather than the actual device user (child). This could be linked to credit card billing information, for example with music downloading on MP3 players.

An example of an implementation is a program in the user's PC 44 with a local connection for independent input of the ICE data, together with access to the operator's or manufacturer's database (54 or 58). This archiving of the data allows it to be restored quickly when a replacement or additional device is used or is desired.

Figure 4A:

FIGS. 4a and 4h illustrate various display screens 70, 80 in accordance with an embodiment of the information access system 25. Referring to FIG. 4*a* various forms of idle screens 71, 72, 73, 74, 75 and 76 are illustrated for various portable devices. Preferably, the ICE idle screens are tailored to the size of the display and the device capability. A small display may only allow the display of the instructions to view the ICE information, as in 71. A display that is slightly wider 72 and/or larger 73 may allow the primary ICE contact to be displayed. An even larger display 74 or 75 allows for ICE information to be displayed together with instructions on viewing the ICE information. As the screen becomes larger, the amount of displayed information, if desired, may be increased. Alternately, should the device user prefer, the ICE idle screen may be set to only display instructions on how to access the ICE information as in 71 or 76. In idle screen 76 the screen cycles through ICE entry 1 through ICE entry N, where N is an integer greater than 1, and allows an ICE entry with full details.

Should the emergency medical team or first responders need additional ICE information (in the case where the first ICE contact is displayed on the ICE Idle screen), they could then follow the instructions and access the ICE information. Referring to FIG. 4*b* various forms of ICE display screens 81*a* and 81*b*, and 82*a* and 82*b* are illustrated for various portable devices. In display screen 81*a* and 81*b*, the screen cycles through ICE entry 1 through ICE entry N. The ICE 1 screen of 81*a* and 81*b* may cycle through alternate telephones of the person displayed, for example showing the cellular number of the wife Abigail 81*a*, then showing her work phone number, and then going to the second ICE contact 81*b*, ICE 2, and similarly cycling through that contact's phone numbers.

A more complex situation is illustrated in 82*a* and 82*b*, where the screen first lists ICE entry selections as shown in 82*a* and allows the selection of an ICE entry with full details as shown in 82*b*. For example, a device owner is on an Alaskan tour. He prefers that his wife be contacted first, the tour guide next, and a friend on the tour third. The device owner may have chosen the ICE idle display of 76, or could have simply chosen the screen of 82*a* as the ICE idle screen. In either event, when the medical or emergency responders reach the screen shown in 82*b* after they have tried his wife, they may be able to conclude based on the location of the emergency (for example, if it occurs in the Los Angeles airport) that he has either completed or not yet started his tour, and look for additional ICE contacts near Los Angeles. They could also see if he has his own contact information stored in ICE and take that into account in their next steps. If, alternately, the emergency occurred in Alaska, they could try and contact the tour guide if they were unable to contact his wife. All of these options that are provided by way of example, illustrate the versatility of the information access system 25.

Figure 5:
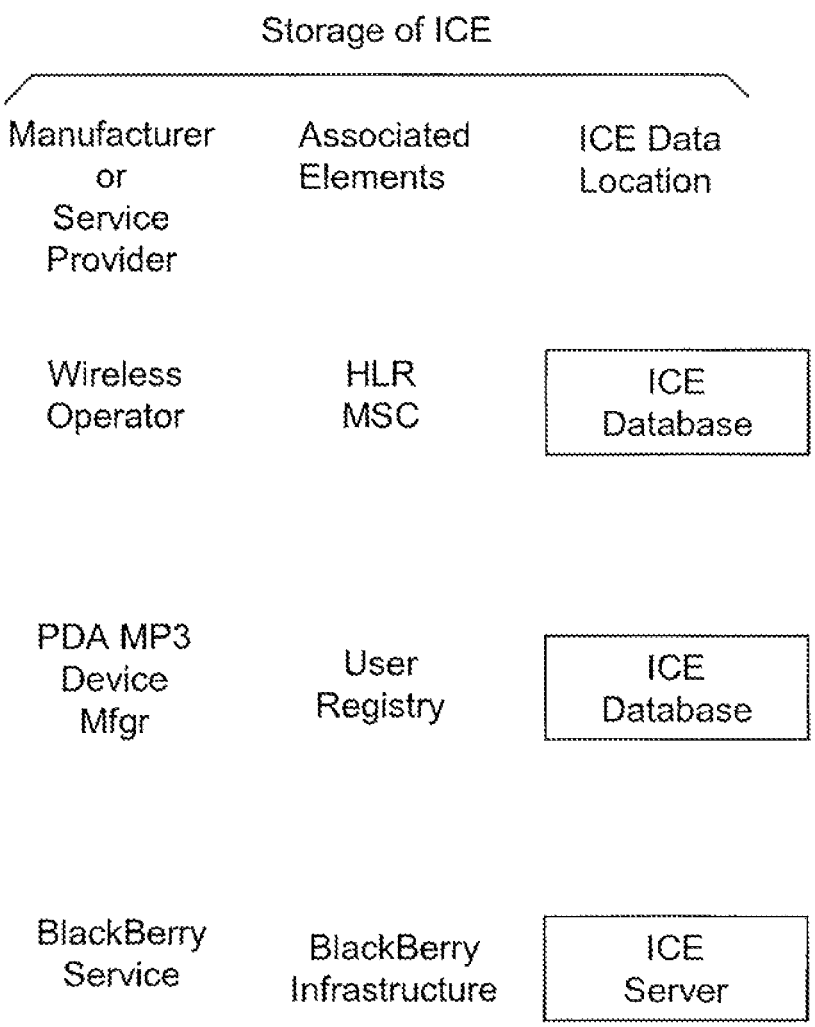
FIG. 5 illustrates an ICE data storage chart for various portable devices, in accordance with an embodiment of the information access system.

Referring to FIG. 5 there is illustrated an ICE data storage chart 90 for various portable devices, in accordance with an embodiment of the information access system 25. Storage of ICE information is dependent upon the type of portable device. Examples are shown for wireless and non-wireless devices. The ICE database may be operated by one or more of a cellular or wireless system operator, a PDA or MP3 manufacturer, the BlackBerry infrastructure, and/or an individual user on user's computer (for backup).

A prime source of ICE data fir emergency responders is the user's portable electronic device. FIG. 5 demonstrates that ICE data may be readily stored in a database, providing both backup (for example, rapid loading of ICE information into a replacement device when the original device fails or is lost) and an alternate source of the data for emergency responders. Devices with keyboard and communications capabilities are also capable of updating the ICE data in these databases.

For a cell phone user, that user's ICE data is associated with (retrievable through) their cellular subscription. Preferably, the subscription information is located in the home location register (HLR) or mobile switching center (MSC). The user of a Wi-Fi™ phone that is registered with a Wi-Fi provider may similarly have their ICE data stored by the service provider and accessible through that registration.

Portable devices that do not have a cellular or similar subscription, such as a PDA or MP3 player or other portable device, may be in the device manufacturer's registry of users. Thus the device manufacture's registry could permit ICE data to be similarly stored in the manufacturer database which would enable the same backup and access for use in replacement devices, etc., as described above for cellular devices.

In a similar manner, BlackBerry devices are identified by a personal identification number (PIN) (and in most cases, also by an International Mobile Equipment Identity (IMEI) or Electronic Serial Number (ESN)). The use of the PIN enables the BlackBerry infrastructure to associate a user's ICE data with the PIN of the user's BlackBerry. Note also that for BlackBerry users, their ICE data may be stored both by the wireless operator and by the BlackBerry service, or by one of them through a coordinated service arrangement.

Figure 6:
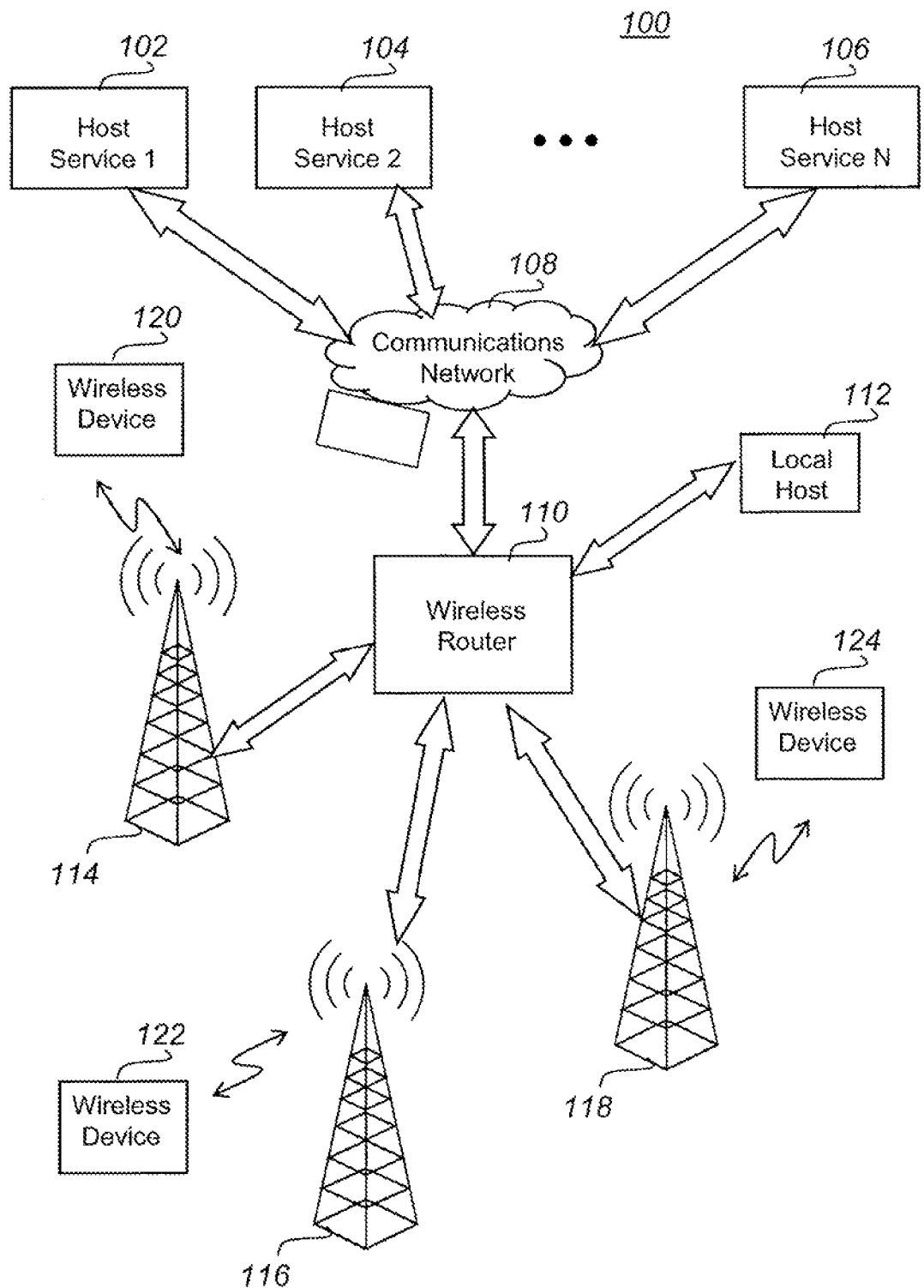
FIG. 6 illustrates in a network diagram a wireless network environment in which exemplary wireless devices can be operated, in accordance with an embodiment of the information access system.

Referring to FIG. 6 there is illustrated in a network diagram a wireless network environment in which exemplary wireless devices can be operated, in accordance with an embodiment of the information access system 25. In FIG. 6, the exemplary wireless communication system 100 includes a plurality of host services (three shown, 102, 104, and 106), each of which may have a plurality of services such as, but not limited to, email, calendar, Internet web browser, and other applications, available to their subscribers. In this particular example, the host services 102, 104, and 106 are typically configured as servers, each containing at least one processor and a storage means, and each using a network interface over which communication with a communication network 108 such as the Internet can be effectuated. The host services 102, 104 and 106 send and receive messages over communications network 108 to and from wireless router system 110 allowing communication between the host services 102, 104, and 106 and the wireless router system 110.

The wireless router system 110 is connected to a plurality of wireless networks (three shown, 114, 116, and 118), each of which may support a plurality of mobile devices (one in each wireless network is shown, 120, 122, and 124). The wireless networks 114, 116, and 118 may be a cellular telephone network, such as a global system for mobile communication (GSM) network, or a code division multiple access (CDMA) network, a two-way paging network, a short range wireless network such as Bluetooth and IEEE 802.11 compliant network, and others. The mobile devices 120, 122, and 124 are devices compatible with the corresponding wireless network.

Mobile communications devices 120, 122 and 124 are two-way communication devices with advanced data communication capabilities having the capability to communicate with other mobile devices or computer systems, such as host services 102, 104, 106, through a network of transceiver stations, including wireless router 111 and communication network 108. The mobile communication devices 120, 122 and 124 may also have the capability to allow voice communication. Depending on the functionality provided, it may be referred to as a data messaging device, a two-way pager, a cellular telephone with data messaging capabilities, a wireless Internet appliance, or a data communication device (with or without telephony capabilities). The preceding list is not meant to be exhaustive the embodiments described herein can be practised with any type of mobile device, whether listed above or not.

One of the primary purposes of host services 102, 104 and 106 is to process information received from other sources, such as mail servers (not shown) and mobile communications devices 120, 122, 124, and send the information on to the appropriate recipient, typically a different host service 102, 104, 106, mail server or mobile communications device 120, 122 or 124. Host services 102, 104 and 106 are configured to send and receive email, messages and as such typically communicate with a mail server. Mail servers could include for example a Microsoft™ Exchange™ server, a Lotus™ Domino™ server, a Novell™ GroupWise™ server, an Internet Message Access Protocol (IMAP) Server, a Post Office Protocol (POP) Server or a webmail server or any other mail server as would be understood by those in the art. The host services 102, 104 and 106 also contain a software module, which executes in their processor to achieve the desired sending and receiving of messages as well as the appropriate processing of information. In one embodiment, the software module of each host service 102, 104, 106 is a messaging module, the messaging module is adapted to receive messages from at least one external mail server, send messages to mobile communications devices, 120, 122, 124, receive messages from the same mobile communications devices and send messages to the at least one external mail server(s). The at least one external mail server(s) could also be at least one mobile data server(s) for example. The wireless router system 110 may also be directly connected to a host service, such as a local service 112, without the communication network 108. In another embodiment, it is possible for host services 102, 104 and 106 to communicate directly with mobile communications devices 120, 122 and 124. In this embodiment, host services 102, 104 and 106 are capable of addressing communications to mobile communications devices 120, 122 and 124 without the aid of the wireless router system 110.

Referring to FIG. 7 there is illustrated an example of mobile communications device 126 for providing ICE information, in accordance with an embodiment of the information access system 25. The mobile communications device 126 may be a cell phone and includes a display screen 128 and a keyboard 130. The keyboard 130 includes a key 132 bearing an ICE indicia. In the present example the ICE indicia is shown as a asterisk having squared points, representative of the "Star of Life" certification mark of the National Highway Traffic Safety Administration (NHTSA) of the United States of America. This symbol has been adopted by emergency medical services organizations around the world, with the star portion being added to other design components in various countries.

In operation, in the event of an emergency, with the owner of the mobile communications device 126 in an unconscious or semi-conscious state, the mobile communications device 126 may be in a locked condition, thereby preventing third parties from accessing phone lists of friends or relatives. When the key 132 hearing a stylized indicia is depressed, ICE information 134 is displayed. The locked display 128 could indicate existence of 'ICE' info by displaying 'ICE' 134 and any symbol chosen to represent the availability of ICE information.

Referring to FIG. 8 there is illustrated another example of a mobile communications device 140 for providing ICE information, in accordance with an embodiment of the information access system 25. The mobile communications device 140 may be an electronic mail device and includes a display screen 142 and a keyboard 144, both of which are larger than the mobile communications device 126 of FIG. 7. The keyboard 144 includes a key 146 hearing a stylized indicia. Such devices with larger displays could provide further information, including directions to display the 'ICE' information.

Figure 9:
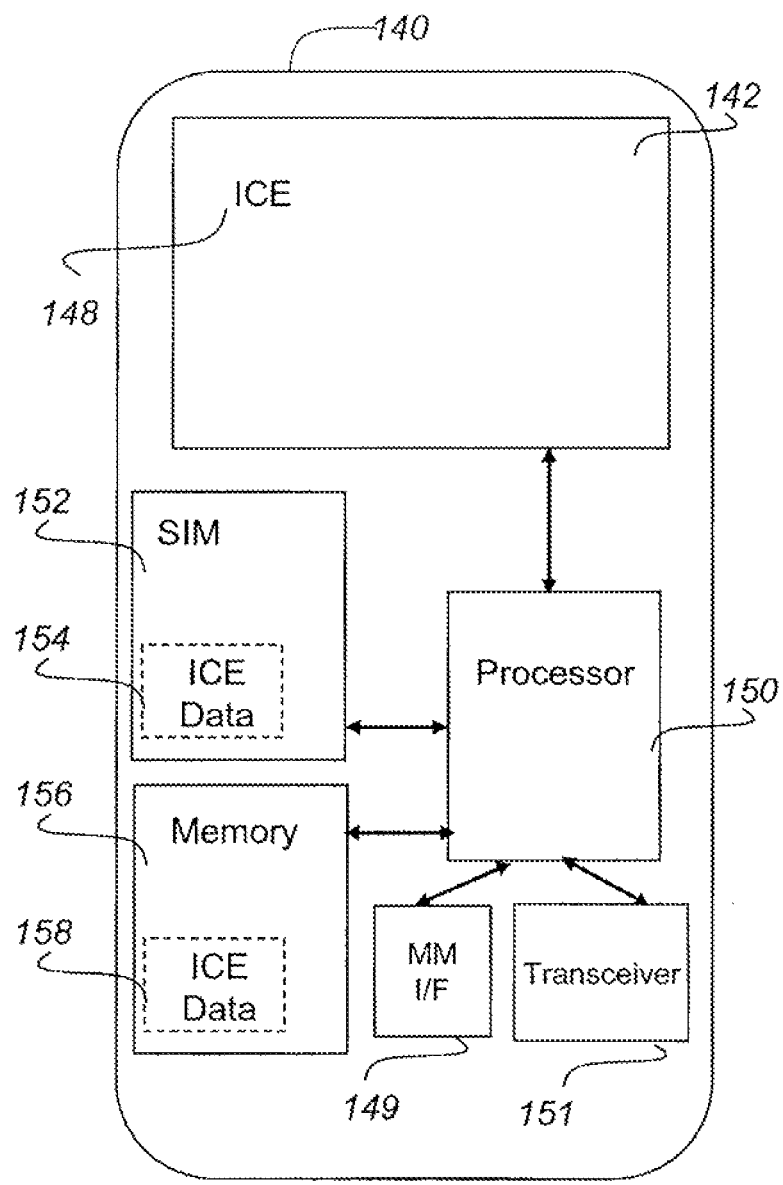
FIG. 9 illustrates a more detailed example of the mobile communications device for providing ICE, in accordance with an embodiment of the information access system.

Referring to FIG. 9 there is illustrated a more detailed example of the mobile communications device 140 for providing ICE, in accordance with an embodiment of the information access system 25. The mobile communications device 140 includes a display screen 142 for displaying ICE information 148, a man-machine interface (MM I/F) 149, a processor 150, a transceiver 151 and a SIM card 152. The SIM card 152 includes ICE data 154. For devices without a SIM card 152, but having a memory 156, ICE data 158 is stored therein for access by the processor 150. The ICE information can be stored in different ways. For example, the ICE information may be stored as a separate list for ICE, or as a portion of a standard phone list with an ICE field added.

Information in portable devices are often locked for security reasons. Preferably, once ICE information is loaded into a portable device, a) there is an indication that the device may be ICE-capable, b) there is ease of access by first responders and emergency personnel, c) there is ease of use (of ICE information), d) there is protection of non-ICE PAB (personal address book) and other information if the device was locked, e) there is separation of the device-locking and the ICE access functions, so that access to ICE does not compromise the basic device and SIM of there is one security.

Man-machine user interface events may be designated to unlock ICE information. For example, pressing a "*" key (asterisk or 'star of life') three or four times, or holding a "*" key (asterisk or 'start of life') for two seconds. Preferably, one of these examples may be used as a standard for all portable devices.

Advantageously, the asterisk has some similar characteristics as the 'star of life', and is common to many keyboards the asterisk is a required key according to 3GPP specification. Pressing four times is a preferred implementation since pressing three times could be used for supplementary service codes according to the 3GPP specifications. It is preferred that there be no adverse effect on the device by use of the ICE access method. To provide an increased ease of use, it is further suggested that, when the device is a cell phone and is in the locked state or idle state (and not accepting supplementary service codes), three "*" (asterisks) or 'star of life' presses also opens the device to the ICE information: such shortened code does not interfere with the potential use of three asterisks for supplementary service codes since these codes can only be entered when the cell phone is in an unlocked state.

As some devices do not have a keypad, there may not be the "*" key available. Examples of such devices include MP3 players and other portable music devices, and cell phones for children that do not have a cell phone keypad but use a specially-adapted user interface. Such devices typically have some form of man-machine interface (for example an iPod™ has a thumb wheel and select button) that allows access to menus. In those cases ICE information can be positioned as a menu item.

Figure 10:
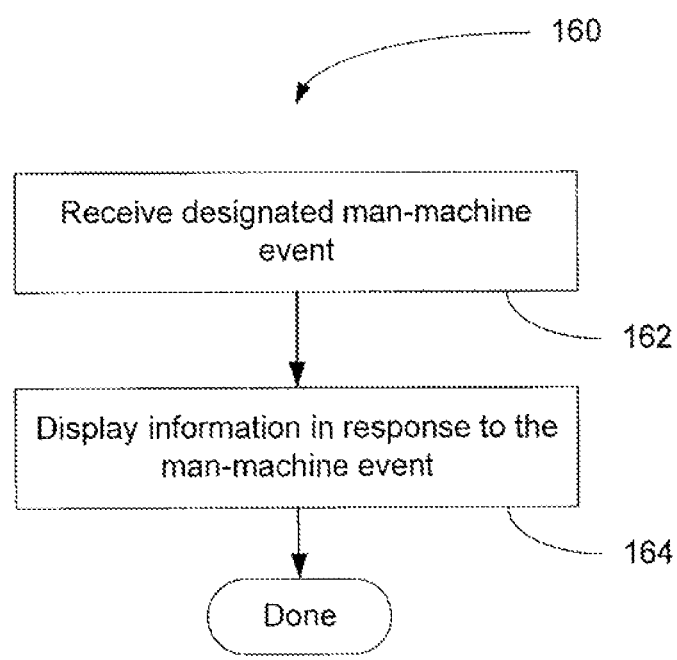
FIG. 10 illustrates in a flowchart an example of obtaining information from a locked mobile device, in accordance with an embodiment of the information access system.

FIG. 10 shows in a flowchart an example of obtaining information from a locked mobile device (160), in accordance with an embodiment of the information access system 25. The method (160) begins with receiving a designated man-machine event (162) (such as pressing the asterisk four times). Next, information is displayed in response to the man-machine event (164). The information is displayed despite the portable device being locked. The method (160) is done. Other steps may be added to this method, including obtaining information from a local or remote repository. The method (160) may be implemented in the processor of the portable device 16 or the man-machine interface module 22. Advantageously, this method may be used to obtain ICE information from the locked device. This method may be used to obtain other information as well. Subsequent examples of embodiments of methods described below recite the term "ICE information". Other information may be suitably used in place of "ICE information".

While most cellular wireless devices now use a SIM or equivalent, some do not. An example of cell phone without a SIM or like module is a CDMA cell phone. (Note that some device models may have a RUIM). An example of a non-cellular wireless device that the user may carry with them is a Wi-Fi phone.

The information access system 25 and method (160) may be implemented in portable devices, including wireless devices, that the user would often carry with them, whether or not a SIM or equivalent is used. For example, the information access system 25 and method (160) may be implemented in cell phones, unlicensed Wi-Fi (wireless LAN) phones, satellite phones (Iridium and others), iPods, PDAs and other portable electronic devices without wireless communications.

Figure 11:
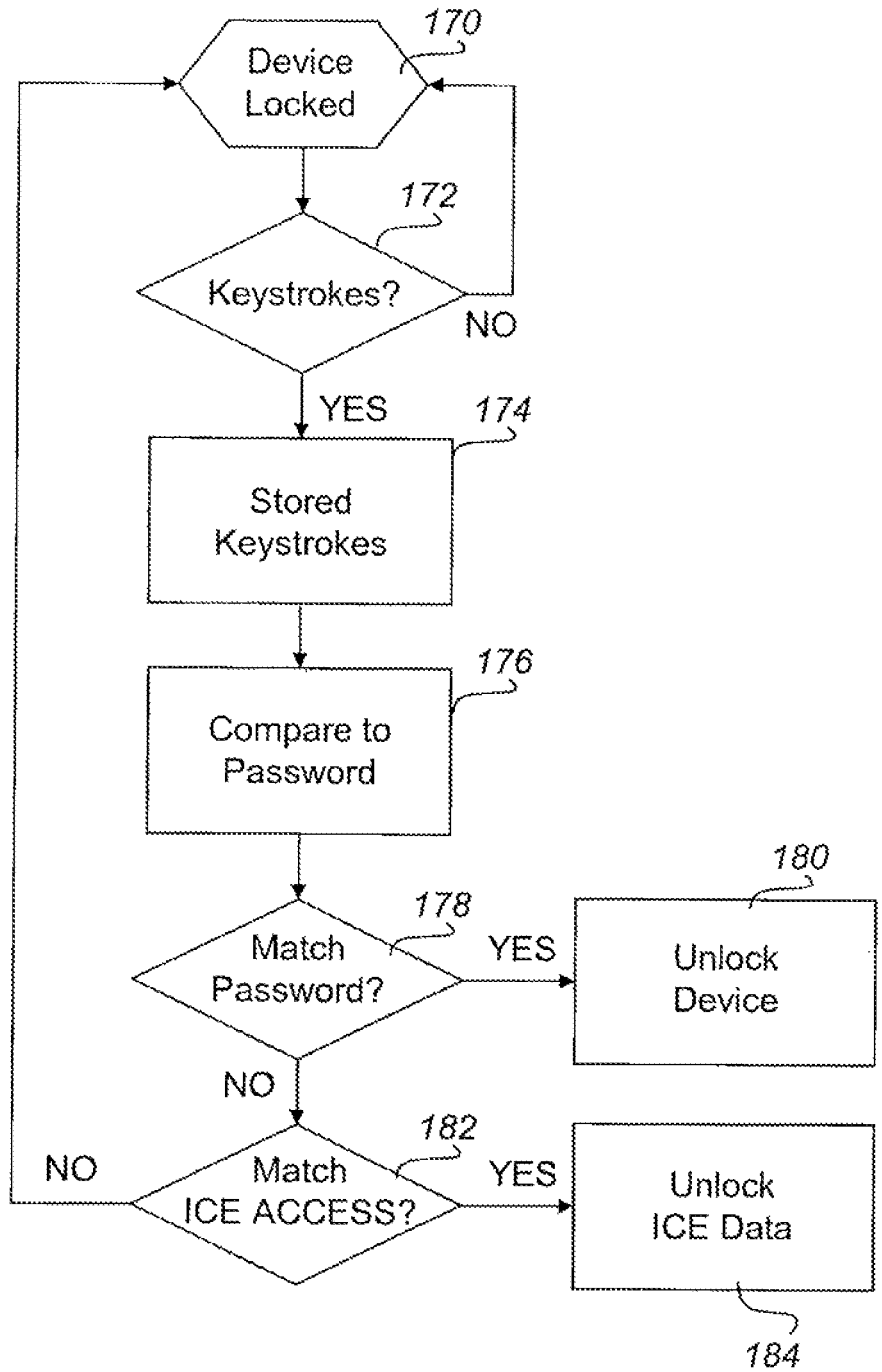
FIG. 11 illustrates in a flowchart an example of a method of unlocking a wireless device for providing ICE, in accordance with an embodiment of the information access system.

Referring to FIG. 11 there is illustrated in a flowchart an example of a method of unlocking a wireless device for providing ICE, in accordance with an embodiment of the information access system 25. A wireless device is locked, as represented by block 170. Keystrokes are detected at decision block 172 and stored at process block 174. The keystrokes are compared to the device users password at process block 176, if matched 178 the device is unlocked as represented by process block 180. If not matched 178, the stored keystrokes are compared to ICE access at decision block 182. If matched 182, access to the 'ICE' information is allowed 184.

Depending upon the portable device age various keystrokes could be used for accessing the information. Preferably, one could use ICE or 423 as the 'unlock' code to display the 'ICE' information, or use '*' key, either repeatedly (say, four times), or holding for an extended period. '*' The indicia may or may not be replaced with a representation of the "Star of Life" as described above.

The locked display would indicate the existence of 'ICE' info by displaying 'ICE' and any symbol chosen to represent it. For example, the 'Star of Life' may be displayed or the representation of 'Star of Life' may be used instead of the on the asterisk key. This could be a six-pointed star, with square ends on the six points or the actual 'Star of Life'.

Devices with larger displays, such as the one shown in FIG. 8 could provide further information, including directions to display the 'ICE' information. Preferably, for new devices, and for those legacy devices where it is possible, the ICE indicia indicates whether there is ICE information in the device. For example, a bold symbol (indicia) would show that there is ICE information, a "greyed-out" symbol would show absence of information. An alert to the user after the end of a trip (date has been reached) can also be displayed. This could be done at each turn-on, or by some other selected algorithm. Preferably, included information that is displayed could include more than a name and phone number according to user preferences.

Figure 12:
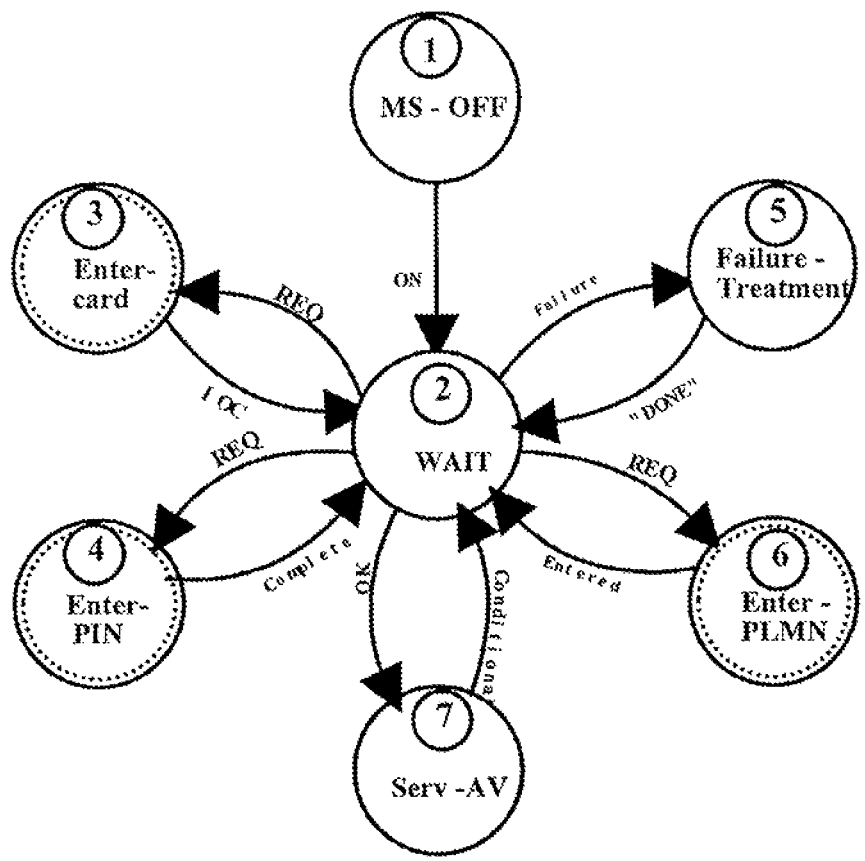
FIG. 12 illustrates in a graph diagram a typical Mealy graph 200 of a user equipment access procedure.

FIG. 12 illustrates in a graph diagram a typical Mealy graph 200 of a user equipment (UE) access procedure. The Mealy graph 200 comprises 7 states that are known in the portable device communication industry: MS-Off (1); Wait (2); Enter-card (3); Enter-PIN (4); Failure-Treatment (5); Enter-PLMN (6); and Serv-AV (7).

Figure 13:
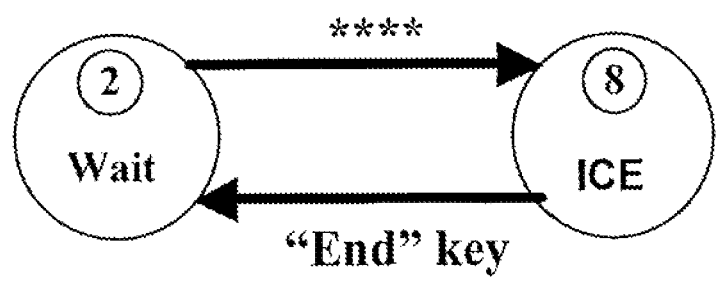
FIG. 13 illustrates in a graph diagram an amendment that can be added to the Mealy graph of FIG. 12, in accordance with an embodiment of the information access system.

FIG. 13 illustrates in a graph diagram an amendment that can be added to the Mealy graph 200 of FIG. 12, in accordance with an embodiment of the information access system 25. An ICE state (8) can be added. A sequence of key strokes (such as 4 '*'s) unlocks the system from the wait (2) state and places the system in the ICE (8) state. Preferably an "end" key is used to exit the ICE state (8) and go back to the wait state (2).

The following is a description of the states of the UE access procedure:
 1) UE-OFF: The UE is in OFF-condition. This means that the equipment is not active as an UE in a PLMN.
 2) WAIT: Waiting for the completion of the UE access conditions, which are related to the type of UE and to the PLMN, where in the UE is roaming (e.g. location updating).
 3) ENTER CARD: Request for entering of the subscriber card, (e.g. when no built in SIM module is available).
 4) ENTER PIN: Request for entering of the correct PIN.
 5) FAILURE TREATMENT: Waiting for removal the actual failure condition.
 6) ENTER PLMN: Request for selection of PLMN.
 7) SERV-AV: The UE is in a ready state. PLMN services are available to the user.
 8) In case of emergency (ICE) The UE is unlocked and ICE information is available. If the UE had been locked in the previous state, then only the ICE information is available The following is a description of the transitions between UE access states
 ON: The equipment becomes active as an UE in a PLMN.
 REQ: A request for user activity.
 IOC: Insertion of a subscriber card with SIM/USIM-module.
 COMPLETE: The PIN has been entered.
 ENTERED: A PLMN choice has been done.
 FAILURE: A failure condition has occurred in any other state during the UE access procedures.
 CONDITIONAL: One of the conditions the UE is waiting for in WAIT state has been lost. The UE goes back to the WAIT state.
 "DONE": The UE access failure condition has been corrected.
 OK: All the conditions the UE is waiting for in the WAIT state are accomplished.
 ICE unlock: The UE enters the in case of emergency (ICE) state.
 "Off" key: The UE goes back to the WAIT state.

Preferably, FIGS. 12 and 13, and the above descriptions of states and transitions define the requirements for a preferred standard for the Man-Machine Interface (MMI) of the user equipment incorporating ICE access procedures. The preferred standard allows anyone to access the ICE information stored on the (U)SIM or on the UE. The use of the procedures in the preferred standard does not make other information (for example, non-ICE entries in the phonebook) visible. The procedure of the preferred standard operate whether or not the SIM PIN is locked and whether or not the handset is locked. In the preferred standard, the unlocking of the mobile device storing ICE information occurs when the mobile device is in an idle state and any alphanumeric key is pressed three times or any alphanumeric key is depressed for two seconds.

The following description describes an example of the storage of ICE information on a SIM card.

Preferably, ICE information is placed on the SIM card. This enables the user (through the operator) to download the information to the SIM (or USIM). The device may or may not make a copy of the ICE information. Preferably, the device makes a copy of the ICE information and retains the copy on the device. New files may be added to the SIM card.

For example, an existing phone address book may have a limited number of fields. Preferably, one or more new files containing the ICE information is used, that has the information and fields to be tailored to ICE use. Preferably, the ICE files alone are unlocked through the use of a mechanism available to emergency responders, and this use of separate files (rather than files or records within existing, general address books) ensures that the ICE unlocking does not unlock or otherwise affect the main address book. Further, this use of separate ICE information files allows the ICE files to evolve. Furthermore, a single standardized approach for new devices can be used.

Although, as implied above, ICE information, can be placed in a newer-style address book file (where ICE information or entries is "integrated" with other conventional address hook entries such that the ICE information can be accessed from a locked or unlocked state while other non ICE-related information in the address book file remain locked when the device is in a locked state), such storage does not provide the basis of a standardized approach where the ICE information is maintained separately from the address hook file. Moreover, having ICE information continue to be identified only by "ICE" in front of the name in the address book entry would prevent the advantages of the separate ICE files from being achieved. Without a standard, each cell phone [or portable device] manufacturer could use different formats and techniques, thereby limiting or preventing easy transfer of a user's ICE information from one handset or device to another handset or device. Advantageously, maintaining ICE information separately from the address hook file and in a standardized form allows for the transfer of the user's ICE information by moving the user's SIM card to the new wireless device. Preferably, a standard is set for ICE information for SIM cards so that the files are placed in a new dedicated file (DF), for example, $DF_{ICE}$. Preferably, this DF would have two elemental files (EFs): a) $EF_{IU}$ (ICE User) and b) $EF_{IC}$ (ICE Contacts).

The ICE User file would provide the [cell phone] user's information:

| | |
|---|---|
| Name | |
| Address | |
| Country | |
| Time Zone | |
| Language(s) | For emergency personnel |
| Phone number | Number split (space) so that the country code is clearly identified |
| Mobile number | Number split (space) so that the country code is clearly identified |
| Traveller's group info | Identifies the User as travelling with a group. Provides the starting and ending date of the tour, so that emergency personnel will know whether it is current. |
| Blood type | |
| Comment | User may wish to add information on medical condition or other instruction for emergency personnel. User may also leave blank. |

The user who travels presents additional issues regarding ICE information. The location that the user visits may have a different language, or both a different language and a different alphabet [for example, Western alphabet vs Japanese, Chinese or other scripts]. The issues may be addressed in several steps.

For travel within countries using a Western alphabet, the field headings may be provided in multiple languages, i.e., user's language and English, or user's language, English, and language of frequently-visited countries. The use of multiple languages in the headers allows the emergency responders to determine which telephone numbers are for work (business), home and mobile. The use of multiple languages in the headers also indicates to the emergency responders the relationship of the ICE contact, i.e., spouse, brother, friend, physician, tour guide. The headings would preferably be pre-programmed in at least the user's language and English with the ability for the emergency responder to choose which language is most useful to them. In this example, the user's ICE information and the contacts' ICE information is entered in the user's native language. With the field headings and the telephone numbers available to, and understood by, the emergency responders, most or all of the goal of ICE information is achieved.

A more difficult situation occurs when the user with a Western language travels to a country with a different alphabet or script. English (and likely to as lesser degree other Western languages) may enable emergency responders to have access to at least the field headings (if a person conversant in that Western language is available) and the telephone numbers. For a user (with a Western language) that will be in a country using a non-Western language for an extended time, it is preferable to have both the field headings and the information within the fields translated to the language of the country so that emergency responders have access to all of the information without the need for a translator. Similarly, a user (with a non-Western language) that will be in a country that uses a Western language would need to have both the field headings and the information within those field translated to English or other appropriate Western language.

Preferably, the provision of field headings in several languages (using both Western and non-Western languages) is available to the user when the ICE information is initially input and when the user's itinerary calls for additional languages. This may be accomplished without knowing the name and details of the user and the user's ICE contacts. The languages that are available are preferably indicated so that the emergency responders may select the most useful language. The case where the names and other details must be translated between Western and non-Western languages can be handled individually.

The user may choose not to provide all information, for example, excluding the street address and city from the address. Preferably, the Traveler's group info dates use an alphabetic abbreviation for the month, so as to prevent misunderstandings. When the Traveler's group info date has expired, the user will be alerted, and asked whether the tour or travel has been completed or has been extended, i.e., (a) delete the traveler's group info for that trip and delete the association with the travel in the contacts entry (and whether that contact should be deleted), or (b) extend the date of the tour or trip in the Traveler's group information.

The ICE Contact file would provide information on the people or groups that emergency personnel may wish to contact.

| | |
|---|---|
| Name | |
| Relationship | Relationship to user. Mom, spouse, brother, friend, physician, travel-group member, tour director, ... |
| Address | (optional) |
| Time Zone | If different from User |
| Country | |
| Language(s) | For emergency personnel |
| Phone number | |
| h | Number split (space) so that the country code is clearly identified |

| | |
|---|---|
| w | Number split (space) so that the country code is clearly identified |
| Mobile number | Number split (space) so that the country code is clearly identified |
| Comments: | Could be used for IM, or for other comments. Could also be used to indicate additional fields have been added. |
| Travelling with user? | Indicates that this contact is travelling with the user |

Headings (when displayed) would preferably be in user's language and English or possibly other second language. The user may choose not to provide all information. Preferably, organizations, such as MedicAlert, would also be included in the contacts. Preferably, the user is able to prioritize the order of the contacts.

The following input techniques can be used for ease of use, insertion and updating of information within the wireless device:
  A. A user enters information online into operator web page. In this scenario the operator maintains database and forwards information OTA (over-the-air) to the SIM.
  B. Optionally, a user may enter information via personal computer (PC)-UE connection and cable.
  C. A user enters information via PC-UE using Bluetooth or other wireless connection.
  D. A user enters information via keyboard (TAP).

To display ICE information on a locked device such as a locked phone, separate DFs and EFs in the SIM are used to store. ICE related information such as the user's home information, contacts, traveler's information and related information separately from the usual address book entries. This segregation of ICE information in specific ICE-oriented files enables the ICE information to be unlocked while the usual address book entries and other data remain locked and inaccessible.

To deal with limited space in each SIM address book entry, 'ICE' information is transferred from SIM/USIM to a mobile equipment (ME).

For the updating of information, the ME manages access to the information.

When a user obtains a new cell phone, the registration or enabling process will alert the user that ICE information should be entered. Should the user place an already registered SIM in the wireless device, the user would preferably be asked if that ICE info (already on the SIM) is accurate and up-to-date.

When a user obtains another SIM, the handset and SIM are synchronized. The SIM may not have the DF and EF 'ICE' files, or it may have the OF and EP 'ICE' files without any information in them. Further, the another SIM may be a permanent SIM for the user (at least for a period of time), or the SIM may be a temporary loan for a (possibly brief) period from an associate or from the user's enterprise. If the SIM does not have any 'ICE' information contained in it, then presumably the information from the handset could be used, and the question "Keep 'ICE' information on <name of user, from ICE info> from the handset, and write to the SIM?" could be prompted to the user. If the user selects 'No', then the user could be prompted to insert 'ICE' information which would be placed in the SIM files and then copied to the handset overwriting the previous information.

Figure 14:
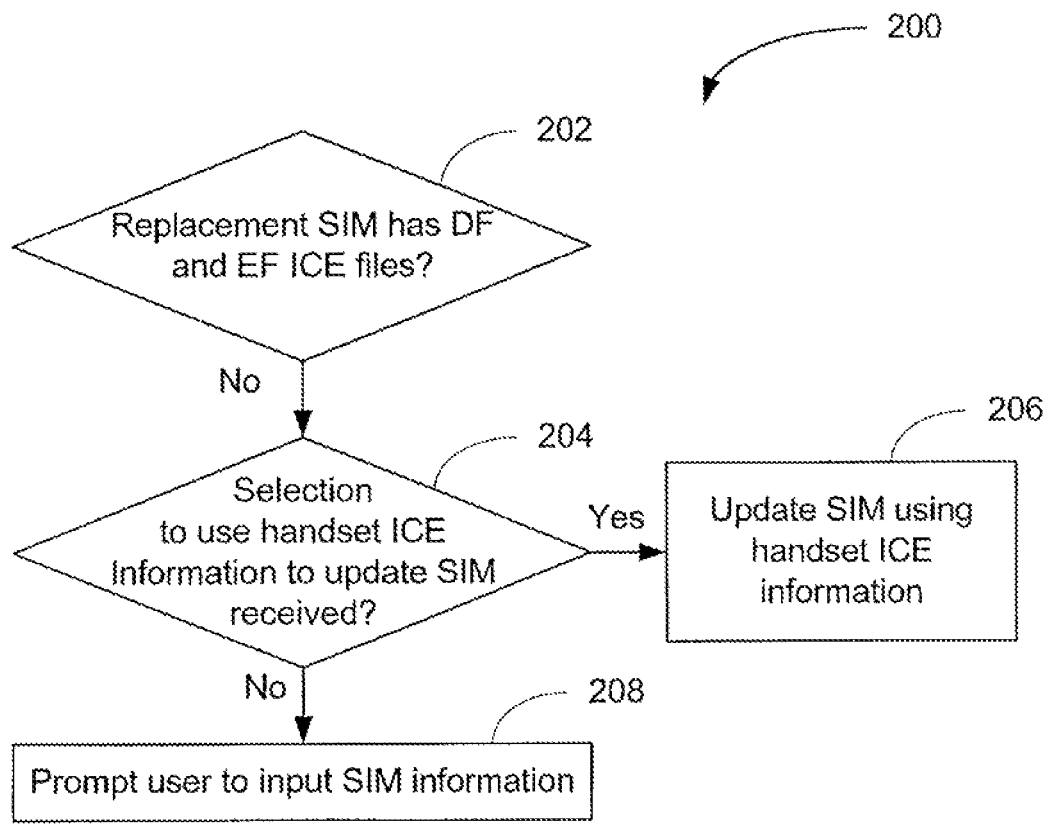
FIG. 14 illustrates in a flowchart an example of a method of synchronizing a handset and SIM, in accordance with an embodiment of the information access system.

FIG. 14 shows in a flowchart an example of a method of synchronizing a handset and a replacement SIM (200), in accordance with an embodiment of the information access system 25. If the replacement SIM does not have the DF and EF ICE file (202), or if the SIM's DF and EF ICE files do not have any information in them (202), then a message is displayed prompting a user to select if the user wishes to update the replacement SIM to reflect the ICE information on the handset (204). If so (204), then the SIM is updated with the information (206). If not (204), then the a message is displayed prompting a user input ICE information to be stored in the SIM (208).

Legacy wireless devices that do not have special indicia can be programmed to access the information via other key strokes. For, example by typing use ICE or 423 as the 'unlock' code to display the 'ICE' information, or by using a '*' key, either repeatedly (e.g., three or four times), or pressing for extended period. The '*' indicia may or may not be replaced with the stylized indicia as described above.

New Devices and new SIMs, USIMs, ISIMs, RUIMs can be produced with the ICE capability built in.

If a legacy SIM is not ICE-enabled, the legacy SIM may have the DF and EFs added via an OTA (over-the-air) command from the operator. Many recent legacy devices are capable of loading games and other applications onto the handset (device). Many handsets are being produced that use Binary Runtime Environment for Wireless (BREW) or Java (or other "standardized" languages) as the programming language for such applications. Thus, operators and manufacturers could produce BREW or Java applications that would enable use of ICE (as described herein) on the device. It is further noted that, with the standardization of BREW, and the industry work towards standardization of Java for many handsets, that a single, e.g., Java ICE, application may be installable on many different models of handsets. The device, once the BREW or Java ICE application is installed, would then operate with the same capability as a handset manufactured with the ICE capability fully installed.

Devices such as the RIM BlackBerry™, having a mode where information is stored on the infrastructure thus enabling change to a new wireless device with the information (from the previous device) downloaded, to the new device, may store the ICE information via the OTA backup. This enables change to a new wireless device even in the case where a SIM card is not used.

The system and methods according to the present disclosure may be implemented by any hardware, software or a combination of hardware and software having the above described functions. The software code, either in its entirety or a part thereof, may be stored in a computer readable memory. Further, a computer data signal representing the software code which may be embedded in a carrier wave may be transmitted via a communication network. Such a computer readable memory and a computer data signal are also within the scope of the present disclosure, as well as the hardware, software and the combination thereof.

While particular embodiments of the patent disclosure have been shown and described, changes and modifications may be made to such embodiments without departing from the true scope of the patent disclosure.

What is claimed is:

1. A portable device capable of providing access to In Case of Emergency (ICE) information, the portable device comprising:
  a man-machine interface;
  a display; and
  a processor coupled to the display and to the man-machine interface, the processor being configured to present through the display at least one ICE entry while the portable device is in a locked condition and in response to a predetermined operation associated with the man-machine interface.

2. The portable device of claim 1, wherein when the portable device is in the locked condition and the at least one ICE entry is accessible, at least some other information in the portable device remains protected.

3. The portable device of claim 2, wherein the processor is configured to display the at least one ICE entry.

4. The portable device of claim 3, wherein the processor is configured to by-pass or over-ride the locked condition to display the at least one ICE entry.

5. The portable device of claim 1, wherein the predetermined operation is a repeated pressing of a key.

6. The portable device of claim 5, wherein the repeated pressing of the key is a repeated selection of a star or asterisk key.

7. The portable device of claim 1, wherein the processor is configured to display the at least one ICE entry regardless of whether or not a SIM personal identification number "PIN" is locked.

8. The portable device of claim 1, wherein the at least one ICE entry is stored in a dedicated file.

9. The portable device of claim 8, wherein the dedicated file comprises an in case of emergency User elemental file and an in case of emergency contact elemental file.

10. The portable device of claim 9, wherein the User elemental file comprises user information comprising one or more of Name, Address, Country, Time Zone, Language(s), Phone number, Mobile number, Travel Information, Medical Information, and Comment.

11. A method for a portable device for providing access to In Case of Emergency (ICE) information, the method comprising:

detecting a predetermined operation associated with a man-machine interface of the portable device when the portable device is in a locked condition; and in response to the predetermined operation, presenting at least one ICE entry while the portable device is in the locked condition.

12. The method of claim 11 wherein when the portable device is in the locked condition and the at least one ICE entry is accessible, at least some other information in the portable device remains protected.

13. The method of claim 11 further comprising displaying the at least one ICE entry.

14. The method of claim 13 further comprising bypassing or over-riding the locked condition to display the at least one ICE entry.

15. The method of claim 11 wherein the predetermined operation is a repeated pressing of a key.

16. The method of claim 15 wherein the repeated pressing of the key is a repeated selection of a star or asterisk key.

17. The method of claim 11 wherein the at least one entry is displayed regardless of whether or not a SIM personal identification number "PIN" is locked.

18. The method of claim 11, wherein the at least one ICE entry is stored in a dedicated file.

19. The method of claim 18, wherein the dedicated file comprises an in case of emergency User elemental file and an in case of emergency contact elemental file.

20. The method of claim 19, wherein the User elemental file comprises user information comprising one or more of Name, Address, Country, Time Zone, Language(s), Phone number, Mobile number, Travel Information, Medical Information, and Comment.

21. The method of claim 19, wherein the contact elemental file comprises contact information comprising one or more of Name, Relationship, Address, Time Zone, Country, Language(s), Home Phone number, Work Phone number, Mobile number, Comments, Travel Information, and Medical Information.

* * * * *